(12) United States Patent
Ha et al.

(10) Patent No.: US 9,119,816 B2
(45) Date of Patent: *Sep. 1, 2015

(54) METHOD FOR PREVENTION OR TREATMENT OF DIABETIC ANGIOGENESIS IMPAIRMENT USING C-PEPTIDE

(71) Applicants: KANGWON NATIONAL UNIVERSITY UNIVERSITY-INDUSTRY COOPERATION FOUNDATION, Gangwon-Do (KR); AMOGREENTECH CO., LTD., Gyeonggi-do (KR)

(72) Inventors: Kwon-Soo Ha, Gangwon-Do (KR); Young-Cheol Lim, Gangwon-Do (KR)

(73) Assignee: AMOGREENTECH CO., LTD., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/987,544

(22) Filed: Aug. 6, 2013

(65) Prior Publication Data

US 2014/0128323 A1    May 8, 2014

Related U.S. Application Data

(60) Provisional application No. 61/680,184, filed on Aug. 6, 2012.

(51) Int. Cl.
| | |
|---|---|
| *A61K 38/16* | (2006.01) |
| *C07K 14/00* | (2006.01) |
| *A61P 3/10* | (2006.01) |
| *A61K 38/17* | (2006.01) |

(52) U.S. Cl.
CPC ............ *A61K 38/1709* (2013.01); *A61K 38/17* (2013.01); *A61K 38/1703* (2013.01)

(58) Field of Classification Search
CPC ... A61K 38/1703; A61K 38/17; A61K 38/16; A61K 38/1709
See application file for complete search history.

(56) References Cited

U.S. PATENT DOCUMENTS 7,855,177 B1 * 12/2010 Wahren et al. .................. 514/5.9

FOREIGN PATENT DOCUMENTS

| GB | 2455186 A | * | 6/2009 | ............ A61K 38/28 |
| KR | 10-2010-0057640 A | | 5/2010 | |

OTHER PUBLICATIONS

Diabetes Mellitus-Merck Manual, from http://www.merckmanuals.com/professional/endocrine_and_metabolic_disorders/diabetes . . . , pp. 1-23, accessed May 28, 2014.*
Martin et al, Abnormal Angiogenesis in Diabetes Mellitus, Medicinal Research Reviews, 2003, 23, pp. 117-145.*
Ido et al, Prevention of Vascular and Neural Dysfunction in Diabetic Rats by C-Peptide, Science, 1997, 277, pp. 563-566.*
Johansson et al, The influence of human C-peptide on renal function and glucose utilization in Type 1 (insulin-dependent) diabetic patients, Diabetologia, 1992, 35, pp. 121-128.*
Human C-peptide, from http://www.sigmaaldrich.com/catalog/product/sigma/c5051?lang=en&region=US, pp. 1-2, accessed Mar. 9, 2015.*
B.-L. Johansson et al., "Beneficial Effects of C-Peptide on Incipient Nephropathy and Neuropathy in patients with Type 1 Diabetes Mellitus." Diabetic Medicine, vol. 17, pp. 181-189, 2000.
M. A. Mosier, "Circulating C-Peptide and Diabetic Retinopathy." Diabetes Research, vol. 1, pp. 151-154, 1984.
S. Chakrabarti et al., "C-Peptide and Retinal Microangiopathy in Diabetes." Experimental Diab. Res., vol. 5, pp. 91-96, 2004.
B.-L. Johansson et al., "Influence of Combined C-Peptide and Insulin Administration on Renal Function and Metabolic Control in Diabetes Type 1." Journal of Clinical Endocrinology and Metabolism, vol. 77, No. 4, pp. 976-981, 1993.
R. Klein et al., "Wisconsin Epidemiologic Study of Diabetic Retinopathy, XII. Relationship of C-Peptide and Diabetic Retinopathy." Diabetes, vol. 39, pp. 1445-1450, Nov. 1990.

* cited by examiner

*Primary Examiner* — Julie Ha
*Assistant Examiner* — Li Ni Komatsu
(74) *Attorney, Agent, or Firm* — Dickstien Shapiro LLP

(57) ABSTRACT

Disclosed are a method and composition for the prevention or treatment of diabetic angiogenesis impairment or diabetic wound-healing impairment, using C-peptide. Found to be able to induce angiogenesis through chemotactic migration of endothelial cells, cell migration to wounded areas, capillary-like network formation, and extracellular signal-regulated kinases 1/2 and Akt phosphorylation and nitric oxide production, C-peptide has prophylactic or therapeutic applications in a broad spectrum of various diabetic complications including diabetic angiogenesis impairment.

13 Claims, 22 Drawing Sheets
(10 of 22 Drawing Sheet(s) Filed in Color)

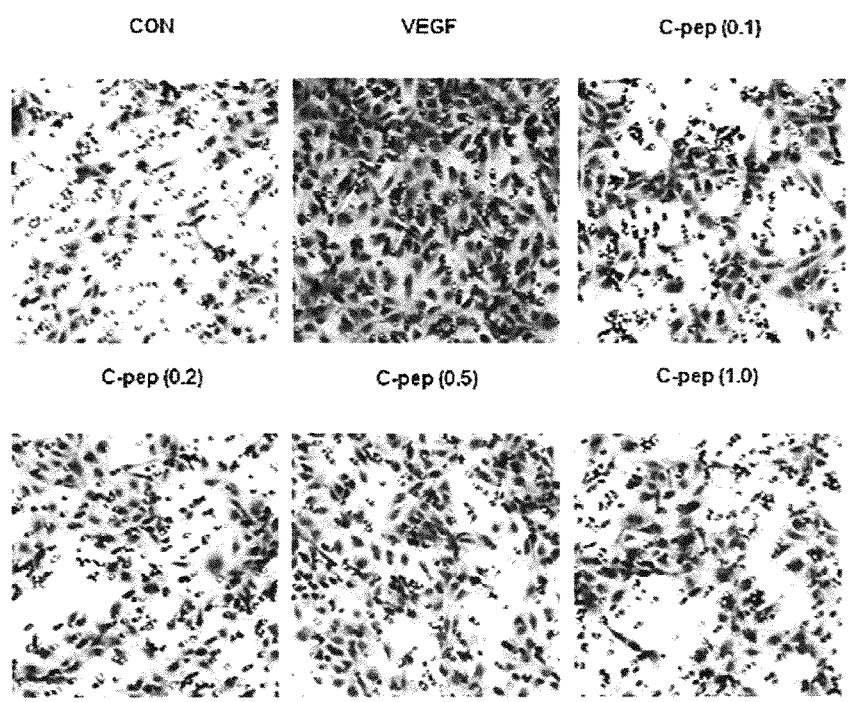

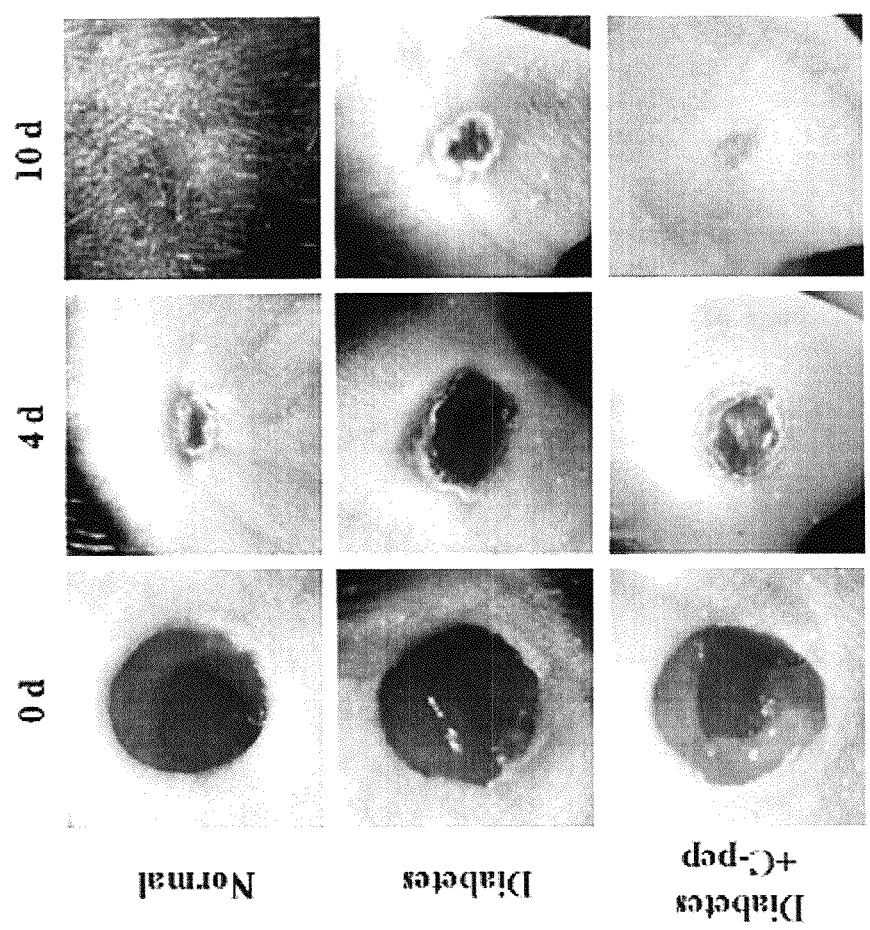

METHOD FOR PREVENTION OR TREATMENT OF DIABETIC ANGIOGENESIS IMPAIRMENT USING C-PEPTIDE

CROSS REFERENCE TO RELATED APPLICATION(S)

This application claims the benefit of U.S. Patent Application Ser. No. 61/680,184, filed on Aug. 6, 2012, which is hereby incorporated by reference in its entirety into this application.

BACKGROUND OF THE INVENTION

1. Technical Field

The present invention relates to the prevention or treatment of diabetes-related diseases using C-peptide. More particularly, the present invention relates to a method for preventing or treating diabetic angiogenesis impairment using C-peptide, a method for preventing or treating diabetic wound-healing impairment using C-peptide, and a composition for use in the prevention or treatment of the impairment, comprising C-peptide.

2. Description of the Related Art

Diabetes mellitus is a group of metabolic diseases with multiple etiologies, characterized by chronic hyperglycemia resulting from the absolute or functional deficiency of insulin activity. A high blood glucose level maintained for a long period of time causes a chronic metabolic disorder and causes damage to blood vessels, with the subsequent onset of various complications. These typically develop after 10 years of diabetes because almost all organs of the body are damaged. Particularly, insufficient angiogenesis is observed in diabetes patients. Angiogenesis is a crucial process for wound healing and the treatment of ischemic tissue injury, but does not normally proceed in diabetes patients. Accordingly, there is a need for a therapy for diabetic angiogenesis disorder, but no noticeable outcome has been reported so far.

These diabetic complications are associated with VEGF (vascular endothelial growth factor). VEGF is known to induce the phosphorylation of ERK1/2 and Akt and the production of NO, promoting angiogenesis, and serve as a vascular leakage factor to incur mascular edema.

Human C-peptide is a short peptide cleaved from proinsulin and is secreted in equimolar concentrations with insulin by pancreatic β-cells into the circulation. Deficiency of C-peptide, along with insulin, is a typical feature of type-1 diabetes mellitus and the later stages of type-2 diabetes mellitus, with the subsequent onset of various complications, including impaired wound healing. Impaired wound healing in diabetes is a serious complication leading to systemic infection, pain, ulceration, and amputation, and may even be fatal.

C-peptide is used for the diagnosis of diabetes, but there have been no reports on noticeable outcomes of the application of C-peptide to the treatment of diabetic angiogenesis disorder.

Under this background, the present inventors conducted intensive and thorough research into the treatment of diabetic angiogenesis impairment, and found that C-peptide can be used for protecting physiological angiogenesis impairment or stimulating wound healing in diabetes, leading to the present invention.

SUMMARY OF THE INVENTION

It is therefore an object of the present invention to provide a method for the prevention or treatment of diabetic angiogenesis impairment using C-peptide, or a composition therefor.

It is another object of the present invention to provide a method for the prevention or treatment of diabetic wound healing impairment using C-peptide, or a composition therefor.

In accordance with an aspect thereof, the present invention provides a method for the prevention or treatment of diabetic angiogenesis impairment, comprising administering an effective amount of C-peptide to an animal in need thereof, that is, to an animal which is prone to being affected by or is affected by diabetic angiogenesis impairment.

In accordance with another aspect thereof, the present invention provides a pharmaceutical composition for the prevention or treatment of diabetic angiogenesis impairment, comprising C-peptide as an active ingredient.

In accordance with a further aspect thereof, the present invention provides a method for the prevention or treatment of diabetic wound healing impairment, comprising administering an effective amount of C-peptide to an animal in need thereof, that is, to an animal which is prone to being affected by or is affected by diabetic wound healing impairment.

In accordance with a still further aspect thereof, the present invention provides a pharmaceutical composition for the prevention or treatment of diabetic wound healing impairment, comprising C-peptide as an active ingredient.

Found to be able to induce angiogenesis, the pharmaceutical composition comprising C-peptide, in accordance with the present invention, has prophylactic or therapeutic applications in a broad spectrum of symptoms requiring angiogenesis for the therapy thereof, such as diabetic wound healing impairment, as well as various diabetic complications including diabetic angiogenesis impairment.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will be more clearly understood from the following detailed description taken in conjunction with the accompanying drawings, in which:

FIG. 1 provides images and graphs showing that C-peptide induces cell migration and wound healing in HUVECs, as analyzed by transwell migration assays (A, B), and by wound healing assays (C, D). HUVECs were seeded on the upper wells of TRANSWELL® Permeable Supports and incubated for 12 h in the presence of 10 ng/ml VEGF or predetermined concentrations of C-peptide (C-Pep) in the lower wells:

FIG. 1A shows images of migrated cells on the lower surface of the filters,

FIG. 2 provides images and graphs showing that C-peptide induces angiogenesis in vitro and in vivo in terms of dose-dependent tube formation (A, B), tube formation (C), and in vivo Matrigel plug assay (D). HUVECs were cultured on Matrigel layers with the indicated concentrations of C-peptide (C-Pep) for 24 h (n=3) (A, B):

FIG. 3 provides images and graphs showing that C-peptide induces ERK1/2 and Akt phosphorylation and NO production in HUVECs.

FIG. 3A shows results of Western blot analysis for phosphorylation of ERK1/2 in which the levels of protein phosphorylation were normalized using the total amount of the proteins and expressed relative to unstimulated control levels (CON), FIG. 3B shows results of Western blot analysis for phosphorylation of Akt in which the levels of protein phosphorylation were normalized using the total amount of the proteins and expressed relative to unstimulated control levels (CON)

FIG. 4 provides graphs showing that various inhibitors prevent tube formation induced by C-peptide and VEGF:

FIG. 5 provides graphs showing that C-peptide repairs diabetes-impaired wound healing:

FIG. 5B is a graph after observing healing of a 4-mm-diameter cutaneous wound using digital photography.

FIG. 6 provides images and graphs showing that C-peptide induces cell migration and VEGF expression in NIH3T3 cells, as measured by transwell migration assays (A, B), and by wound healing assays (C, D). In FIGS. 6A and 6 b, NIH3T3 cells were seeded on the upper wells of TRANSWELL® Permeable Supports and incubated for 12 h in the presence of 1 ng/ml FGF-2 or the indicated concentrations of C-peptide (C-Pep) in the lower wells:

FIG. 6A shows images of migrated cells on the lower surface of the filters,

FIG. 7 provides images showing that C-peptide increases hair follicles regeneration and blood vessel formation around the wound bed:

DESCRIPTION OF THE PREFERRED EMBODIMENTS

Leading to the present invention, intensive and thorough research into prevention and treatment of dysregulation of angiogenesis and subsequent impaired wound healing in diabetes patients resulted in the finding that C-peptide can activate angiogenesis in vitro and in vivo by inducing endothelial cell migration and stimulating capillary-like networks formation, both indispensible for angiogenesis; and that C-peptide stimulates angiogenesis through signaling pathways responsible for ERK1/2 and PI3K/AKT phosphorylation and NO production, and the signaling pathways take part in C-peptide-induced angiogenesis. Also found is the prophylactic or therapeutic effect of the C-peptide induced angiogenesis on diabetic wound healing impairment.

Thus, the present invention pertains to a method or a composition for the prevention or treatment of a diabetic angiogenesis impairment using C-peptide; and a method or a composition for the prevention or treatment of diabetic wound healing impairment.

In accordance with one aspect thereof, the present invention addresses a method for the prevention or treatment of diabetic angiogenesis impairment using C-peptide, or a composition therefor.

More particularly, the present invention provides a method for preventing or treating diabetic angiogenesis impairment, comprising administering an effective amount of C-peptide to an animal in need thereof. Also, the present invention provides a pharmaceutical composition for the prevention or treatment of diabetic angiogenesis impairment, comprising C-peptide as an active ingredient.

Figure 1B:
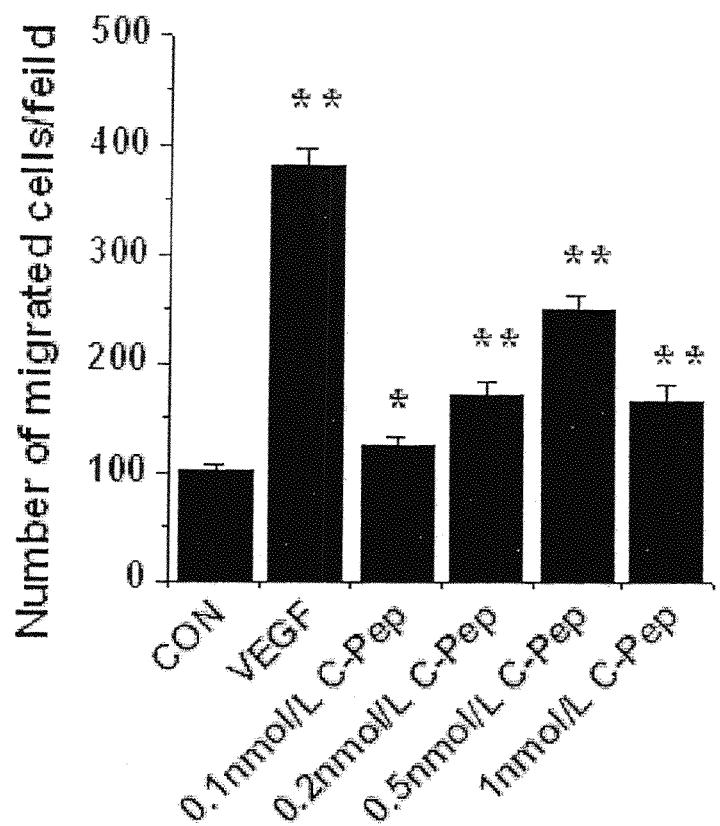
FIG. 1B is a graph in which chemotactic migration is quantified by counting the migrated cells (n=3)
Figure 1C:
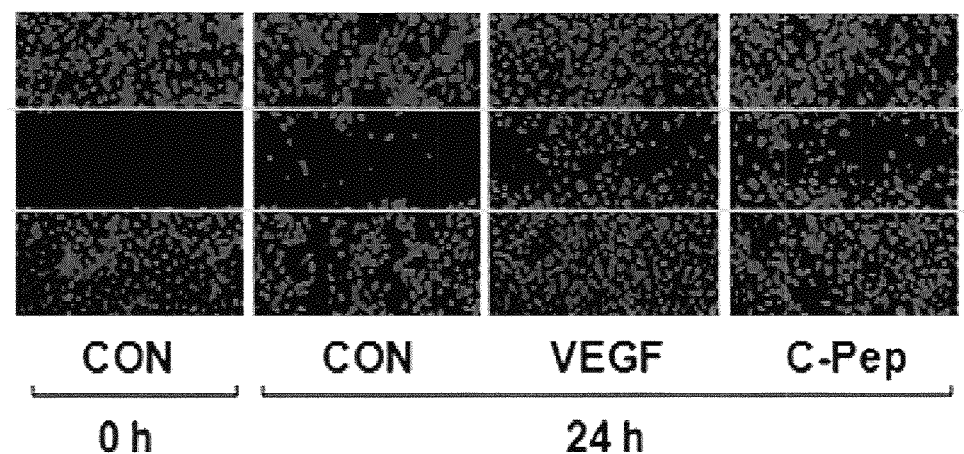
FIG. 1C shows confocal microscopic images of confluent cell layers which were wounded and incubated with 10 ng/ml VEGF or 0.5 nM C-peptide for 24 h.
Figure 1D:
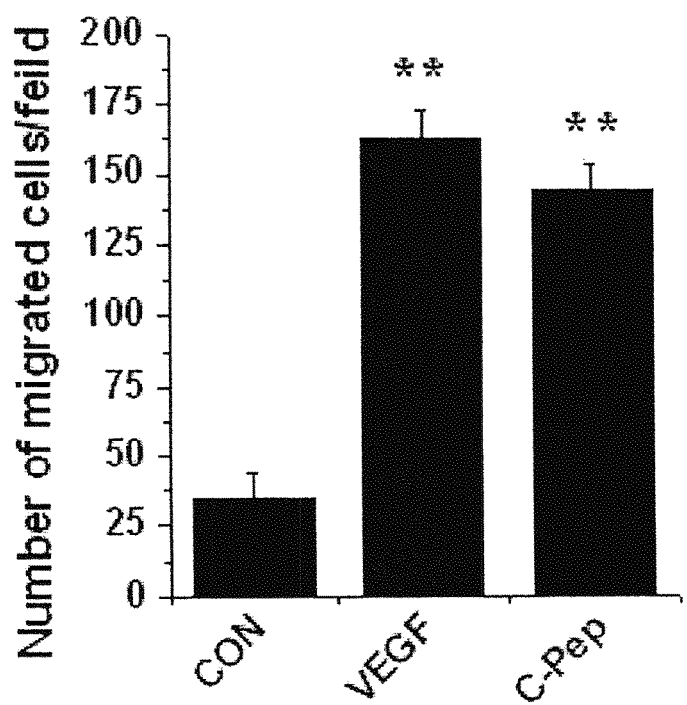
FIG. 1D is a graph in which cell migration is quantified by counting cells that migrated to the scratched area (n=3), and results are expressed as mean±S.D. from three independent experiments. *$p<0.05$, **$p<0.01$. CON, control.
Figure 2A:
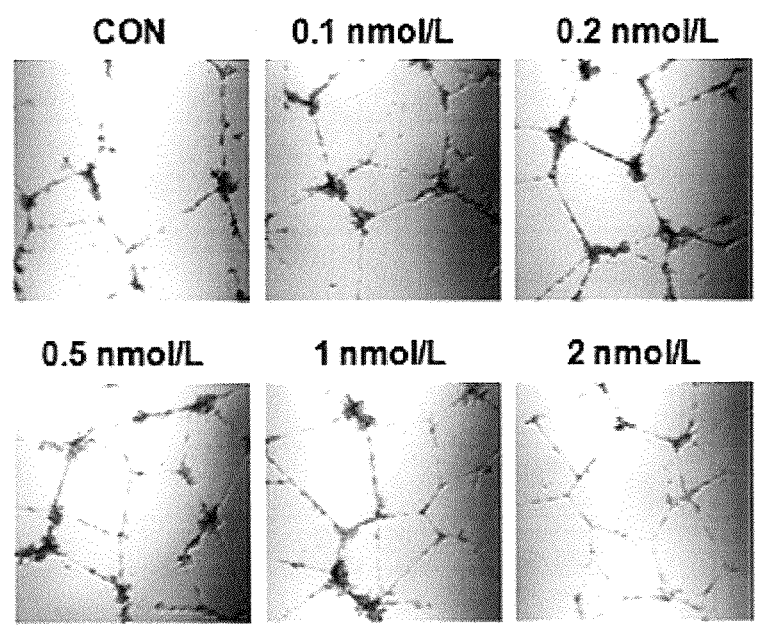
FIG. 2A shows confocal microscopic images of tube formation.
Figure 2B:
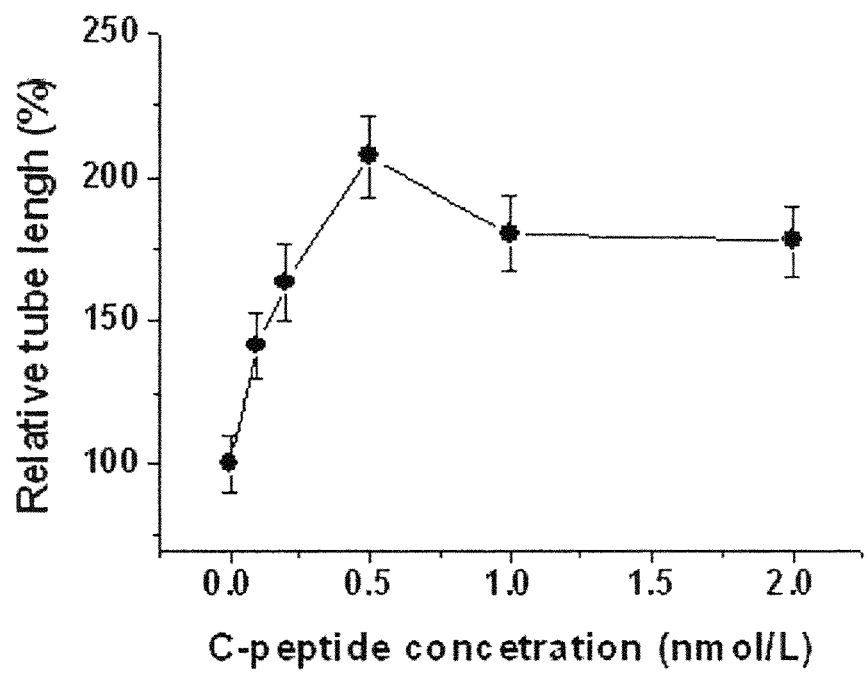
FIG. 2B is a graph in which relative tube length (%) is determined by measuring the tube length from the images in FIG. 2A to examine C-peptide-induced, dose-dependent tube formation.
Figure 2C:
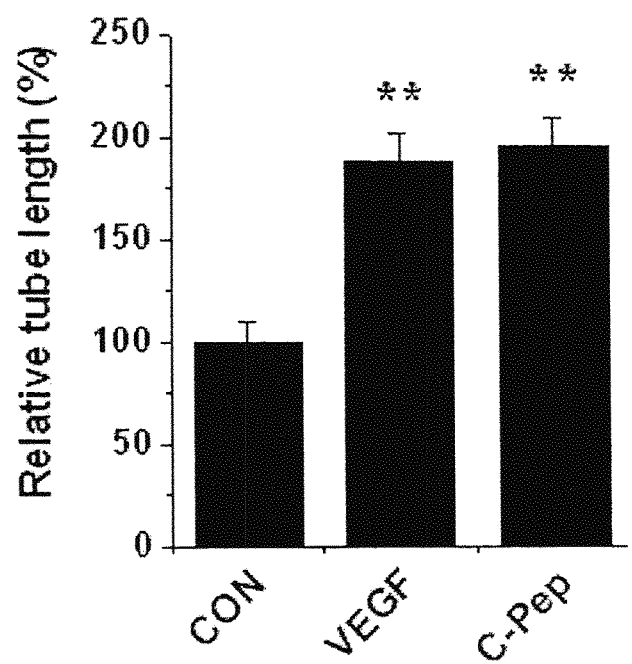
FIG. 2C is a graph showing the tube formation induced by 10 ng/ml VEGF or 0.5 ng/ml C-peptide.
Figure 2D:
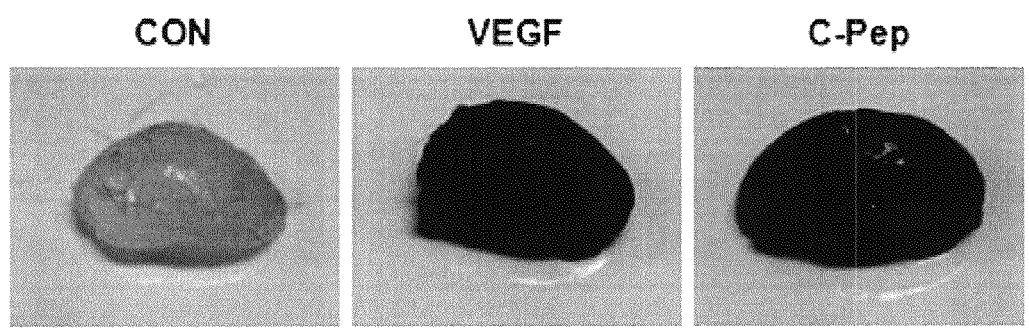
FIG. 2D shows photographs of Matrigels after in vivo Matrigel plug assay in which mice were infected subcutaneously for 7 d with 0.5 ml Matrigel containing 100 ng/ml VEGF or 5 nM C-peptide (n=8 per group).

In the present invention, it was observed that C-peptide causes a dose-dependent increase in the chemotactic migration of vascular endothelial cells and fibroblasts (FIGS. 1A, 1B, 6A and 6B), stimulates cell migration to wounded areas (FIGS. 1C, 1D, 6C and 6D), and induces capillary-like networks formation in a dose-dependent manner (FIGS. 2A and 2B), and the formation of new blood vessels in Matrigel (FIG. 2D). In addition, an experiment demonstrated that C-peptide stimulates vascular angiogenesis, in parallel with VEGF, through the phosphorylation of ERK1/2 and Akt, and NO production in HUVECs (FIG. 3). In accordance with the present invention, therefore, C-peptide or a composition comprising the same can be used in a method or a pharmaceutical composition for the prevention or treatment of diabetic angiogenesis impairment. The prophylactic or therapeutic effect of the C-peptide or composition of the present invention on angiogenesis impairment can be applied to any animal, including humans, that might undergo diabetic angiogenesis impairment.

As used herein, the term "C-peptide" refers to a short protein constituent of proinsulin, found in mammals and birds, which is produced by pancreatic β-cells in the islets of Langerhans. Its length varies from 21 to 31 amino acids depending on its sources. Mammalian C-peptides from various mammals including dogs, cats, rats, chimpanzees, mice, cow, etc. as well as human C-peptide, and avian C-peptide from, for example, thrushes, fall within the scope of the present invention.

For instance, all the C-peptides originating from humans (*Homo sapiens*, SEQ ID NO: 1), rats (*Rattus norvegicus*, SEQ ID NO: 2) and chimpanzees (*Pan troglodytes*, SEQ ID NO: 3) are composed of 31 amino acids while C-peptide is found as a 29-mer peptide in mice (*Mus musculus*, SEQ ID NO: 4), as a 26-mer peptide in cattle (*Bos taurus*, SEQ ID NO: 5), and as a 21-mer peptide in thrushes (*Turdus merula*, SEQ ID NO: 6) and red-footed boobies (*Sula sula*, SEQ ID NO: 7). The C-peptide of the present invention may have an amino acid sequence selected from the group consisting of SEQ ID NOS: 1 to 7.

For the purpose of the present invention, the C-peptide is employed as an active ingredient in the method or the composition provided by the present invention. The method or the composition may be applied to any animal that may be affected by a diabetic angiogenesis impairment-caused disease, as well as humans. In this context, C-peptide is preferably applied to an animal of its origin. For example, if it is applied to humans, the method or the composition of the present invention preferably comprises the C-peptide of human origin (SEQ ID NO: 1).

In one embodiment of the present invention, C-peptide is found to induce angiogenesis in diabetic model mice, so that C-peptide or a composition comprising C-peptide is applicable to the prevention or treatment of diabetic angiogenesis impairment. As used herein, the term "diabetic angiogenesis impairment" means diabetes-caused impaired angiogenesis itself or a disease caused by diabetic angiogenesis impairment which may be selected from the group consisting of stroke, renal diseases, cardiac diseases, foot ulcer, and a combination thereof.

In detail, the prophylactic or therapeutic effect of the method or composition of the present invention on diabetic angiogenesis impairment-caused diseases may be attributed to at least one of C-peptide's activities to induce chemotatic migration of endothelial cells, cell migration to wounded areas, capillary-like network formation, and ERK1/2 and Akt phosphorylation and NO production.

Accordingly, the method or composition of the present invention may be applied to the prevention or treatment of the diabetic angiogenesis impairment following the onset of various diabetic complications, which occurs in any diabetes patient, whether animal or human.

The composition of the present invention is a pharmaceutical composition which may further comprise a pharmaceutically acceptable vehicle, excipient or diluent. The term "pharmaceutically acceptable vehicle, excipient or diluent," as used herein, is intended to include any and all solvents, dispersing media, coating agents, adjuvants, stabilizers, preservatives, anti-bacterial and anti-fungal agents, isotonic agents, and absorption delaying agents. Examples of the vehicle, excipient or diluents useful in the present invention include lactose, dextrose, sucrose, sorbitol, mannitol, xylitol, maltitol, glucose, glycerin, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, mineral oil, etc.

Using a conventional method, the pharmaceutical composition of the present invention may be formulated into oral dosage forms such as powders, granules, tablets, capsules, suspensions, emulsions, syrups and aerosols, or into sterile injections. For the formulation of the composition according to the present invention, diluents or expedients, such as fillers, thickeners, binders, humectants, disintegrants, and surfactants, are commonly used. Solid formulations for oral dosage include tablets, pills, powders, granules, and capsules. These solid formulations are prepared with a lecithin-like emulsifier in combination with at least one expedient such as starch, calcium carbonate, sucrose, lactose, or gelatin.

In addition to the expedient, a lubricant, such as magnesium, stearate, talc, etc. can be used. Liquid formulations for oral administration include suspensions, internal solutions, emulsions, and syrups. In these liquid formulations, various expedients such as humectants, sweeteners, and preservatives, as well as simple diluents such as water and liquid paraffin may be contained. Formulations for non-oral dosage may be typified by sterile aqueous solution, non-aqueous solutions, suspensions, emulsions, lyophilized agents, and suppositories. For non-aqueous solutions and suspensions, vegetable oils such as propylene glycol, polyethylene glycol and olive oil, or injectable ester such as ethyloleate may be used.

So long as it leads to a target tissue, any administration route, whether orally or non-orally, may be adopted for the method or composition using C-peptide in accordance with the present invention. Preferable is subcutaneous injection using an osmotic pump, intradermal injection, intravenous injection, intraperitoneal injection or intravitreal injection.

In the present invention, C-peptide may be administered in an "effective amount," or "pharmaceutically effective amount." The term "effective amount," or "pharmaceutically effective amount," as used herein, means an amount sufficient to afford a prophylactic or therapeutic effect without incurring a significant or undue immune response. It is determined depending on various factors known in the pharmaceutical or medical field, including kind and severity of disease, drug activity, administration route, discharge ratio, administration period of time, co-administered or combined other drugs, patient's age, weight, sex, diet habit, health state, etc. Various factors that are taken into consideration in determining "effective amount," or "pharmaceutically effective amount" are known to those skilled in the art, and for instance, explained in Gilman et al., eds., Goodman And Gilman's: The Pharmacological Bases of Therapeutics, 8th ed., Pergamon Press, 1990, and Remington's Pharmaceutical Sciences, 17th ed., Mack Publishing Co., Easton, Pa., 1990.

The composition of the present invention may be administered alone or in combination with other therapeutics. The co-administration of the composition of the present invention and other therapeutics may be carried simultaneously or sequentially. Single- or multi-dosages are possible. It is important to use the composition in as minimal an amount as possible to sufficiently obtain the greatest therapeutic effect without side effects, which can be readily determined by those skilled in the art. In addition, the administration of the composition may be conducted using a device which helps the active ingredient direct toward target cells.

In accordance with another aspect thereof, the present invention addresses a method and a composition for the prevention or treatment of diabetic wound healing impairment, using C-peptide. More particularly, the present invention provides a method for preventing or treating diabetic wound healing impairment, comprising administering an effective amount of C-peptide to an animal in need thereof. Also, the present invention provides a pharmaceutical composition for the prevention or treatment of diabetic wound healing impairment, comprising C-peptide as an active ingredient.

As described above, C-peptide was found to effectively treat diabetic wound healing impairment as demonstrated in diabetic model mice in the following working Example 2, so that C-peptide or a composition comprising C-peptide is applicable to the prevention or treatment of diabetic wound healing impairment. The prophylactic or therapeutic effect of C-peptide on diabetic wound healing impairment can be applied to humans as well as to any animal that could be affected by diabetes. As used herein, the term "diabetic angiogenesis impairment" means diabetes-caused impaired angiogenesis itself or a disease caused by diabetic angiogenesis impairment which may be selected from the group consisting of strokes, renal diseases, cardiac diseases, foot ulcers, and a combination thereof.

The terms "C-peptide" "dosage", "administration", and "effective amount (pharmaceutically effective amount)" used in the context of the prophylaxis or therapy of diabetic retinopathy are as described in the previous aspect of the present invention.

Particularly, for the prophylaxis or therapy of diabetic retinopathy, the composition of the present invention, or C-peptide may be administered at a single dose of from 2.4 µg to 60 µg and preferably at a single dose of 18 µg via an intrevitreal or interadermal route, or at a rate of from 1.45 pmol/kg/min to 36.5 pmol/kg/min using a mini-osmotic pump. However, the amount is not limited to those ranges, but may vary within the total daily dose, depending on patient's age, weight, sex, health state and diet, the time of administration, the route of administration, the rate of excretion, and the severity of disease.

In detail, the prophylactic or therapeutic effect of the method or composition of the present invention on diabetic angiogenesis impairment may be attributed to at least one of C-peptide's activities to induce chemotatic migration of endothelial cells, cell migration to wounded areas, capillary-like network formation, and ERK1/2 and Akt phosphorylation and NO production.

The terms "C-peptide" "dosage", "administration", and "effective amount (pharmaceutically effective amount)" used in the context of the prevention or treatment of diabetic angiogenesis impairment or diabetic wound healing impairment are as described in the previous aspect of the present invention.

A better understanding of the present invention may be obtained through the following examples which are set forth to illustrate, but are not to be construed as limiting the present invention.

Example 1

Preparation of Experiment

Example 1-1

Experimental Animals

Male C57BL/6 mice, six weeks old, were purchased from Nara Biotech (Seoul, Korea). The mice were maintained in temperature-controlled clean racks with a 12-h light/dark cycle. All experiments were performed in accordance with the guidelines of the Institutional Animal Care and Use Ethics Committee of Kangwon National University.

Example 1-2

Cell Culture

HUVECs were isolated from the human umbilical cord vein according to a well known process, and cells from passages 3 to 6 were used in the following experiments. Cells were inoculated into M199 culture media (supplemented with 20% FBS, 3 ng/ml bFGF, 5 U/ml heparin, 100 U/ml penicillin, and 100 µg/ml streptomycin) in 2% gelatin-coated coverslips, dishes, or plates, and grown at 37° C. in a humidified 5% CO2 incubator.

NIH3T3 fibroblasts obtained from ATCC (American Type Culture Collection) were grown in a DMEM medium supplemented with 10% calf serum, 100 U/ml penicillin, and 100 µg/ml streptomycin.

For experiments, cells were serum starved for 6 h by incubation in low-serum medium (M199 supplemented as above, but with only 1% FBS), and treated for a suitable time with 10 ng/ml VEGF in the presence or absence of various concentrations of C-peptide.

NIH3T3 cells were serum starved for 12 hrs in a low-serum medium (DMEM supplemented as above, but with only 0.1% calf serum).

Example 1-3

Statistical Analysis

Data obtained in each Example was processed and graphically presented using Origin 6.1 (OriginLab, Northampton, Mass., USA). Statistical significance was determined using the t-test and ANOVA. A p-value of less than 0.05 was considered statistically significant.

Example 2

Effect of C-Peptide on Angiogenesis

Example 2-1

Transwell Migration Assay

Angiogenesis is accompanied by endothelial cell migration and capillary-like network formation. To evaluate the ability of C-peptide to induce angiogenesis by examining whether C-peptide stimulates endothelial cell migration, the chemotactic motility of HUVECs and NIH3T3 cells were assayed using TRANSWELL® Permeable Supports (Costar, Corning, N.Y.).

In detail, the lower surface of the filters was coated with 5 µl of 2% gelatin. Low-serum media containing VEGF, FGF-2 or C-peptide were placed in the lower wells. HUVECs or NIH3T3 cells were seeded at a density of $1\times10^5$ cells per 200 µl of the low-serum medium in each of the upper wells, and incubated at 37° C. for 12 h. Cells were fixed with 100% methanol for 15 min, stained with hematoxylin and eosin, and dried. The average number of migrated cells in three randomly chosen fields of view per insert was taken to quantify the extent of migration using a fluorescence inverted microscope (Olympus).

The results are shown in FIGS. 1A and 1B. As is understood from the results, C-peptide induced a dose-dependent increase in the chemotactic migration of endothelial cells, with a maximal effect at 0.5 nM (FIGS. 1A and B).

Example 2-2

Wound Healing Assay

Through a wound healing assay, an examination was made of the effect of C-peptide on angiogenesis.

HUVECs and NIH3T3 cells were cultured on 6-well culture plates coated with gelatin. After being obtained, confluent cell layers were starved with low-serum media for 6 h, stained with 1 µM calcein-AM for 30 min, and wounded with a plastic scraper. Low-serum media and cell debris were removed, followed by replenishing the cell culture with 2 ml of low-serum media containing VEGF or C-peptide. Cells were then incubated at 37° C. for 24 h. Migrated cells was counted from images obtained using a confocal microscope (FV-300, Olympus).

The results are given in FIGS. 1C and 1D. As shown in FIGS. 1C and 1D, C-peptide (0.5 nM) significantly stimulated cell migration to the wounded area ($p<0.01$).

As reported previously, VEGF also stimulated chemotactic migration and wound healing in endothelial cells ($p<0.01$; FIG. 1).

Thus, C-peptide stimulates endothelial cell migration, which is essential for angiogenesis.

Example 3

Tube Formation Assay

To examine whether C-peptide can activate angiogenesis in vitro, a tube formation assay was conducted in a Matrigel layer using HUVECs.

The formation of capillary-like networks by HUVECs on growth factor-reduced Matrigel (BD Biosciences, Franklin Lakes, N.J.) was achieved using a method known in the art. Briefly, 24-well culture plates were coated with Matrigel according to the manufacturer's instructions. HUVECs were seeded onto a layer of Matrigel at a density of $4\times10^5$ cells/well, and treated with VEGF or C-peptide at 37° C. for 24 to 30 h. The degree of tube formation was quantified by measuring the length of tubes from the images using the FV-300 software. The results are given in FIGS. 2A, 2B and 2C.

Consistent with the results of the cell migration assay of Example 2, C-peptide stimulated the formation of capillary-like networks in a dose-dependent manner, with the maximal effect at 0.5 nM (FIGS. 2A and 2B). VEGF induced the formation of capillary-like networks, with similarity to the effect of C-peptide (FIG. 2C).

Thus, it was confirmed that C-peptide activates endothelial cell migration and the formation of capillary-like networks, which are essential for angiogenesis in vitro.

Example 4

In Vivo Matrigel Plug Assay

A matrigel plug assay was used to examine whether C-peptide can induce angiogenesis in vivo. In this regard, in vivo Matrigel plug assays were performed according to a method known in the art.

Briefly, mice were injected subcutaneously with 0.5 ml of Matrigel containing 100 ng/ml VEGF or 5 nM C-peptide, and 10 U heparin. After 7 days, the Matrigel plugs were removed from the subcutaneous region, and photographed using a camera (Sony, Japan). The results are given in FIG. 2D.

One week after Matrigel plug implantation, Matrigel containing C-peptide revealed significantly higher induction of new blood vessel formation, compared with the control, and this result was similar to that seen upon VEGF treatment (FIG. 2D).

Accordingly, these results indicate that C-peptide activates vascular angiogenesis in vitro and in vivo.

Example 5

C-Peptide-Associated Intracellular Signaling Pathway

Example 5-1

Effect of C-peptide on ERK1/2 and Akt Phosphorylation

Since the activation of ERK1/2 and Akt is critical for the induction of cell migration and tube formation, an examination was made of the effect of C-peptide on ERK1/2 and AKT phosphorylation in HUVECs.

Phosphorylation of ERK1/2 and Akt was determined by Western blot analyses. Briefly, HUVECs were scraped off with ice-cold lysis buffer (50 mM Tris-HCl, pH 7.5, 1% Triton X-100, 150 mM NaCl, 1 mM EDTA, 0.1 mM PMSF, 10 µg/mL aprotinin, and 10 µg/mL leupeptin) and centrifuged at 18,000 g for 10 min at 4° C. The resulting cell lysates were separated by SDS-PAGE and transferred to polyvinylidene fluoride membranes.

Protein bands were visualized by exposure to X-ray films and a chemiluminescent substrate (Pierce, Rockford, Ill.). Levels of protein phosphorylation were normalized using the total amount of the proteins, and are expressed relative to unstimulated control levels (CON) in FIGS. 3A and 3B.

Figure 3A:
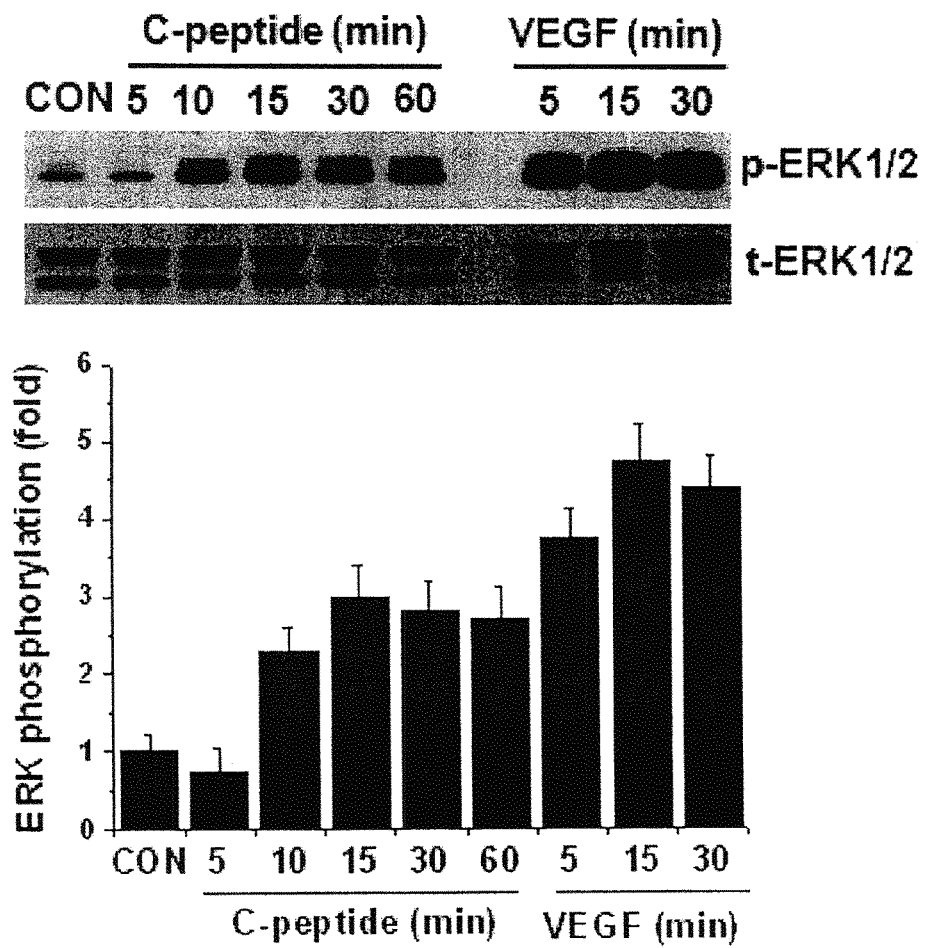
FIGS. 3A and 3B show results after HUVECs were treated with 10 ng/ml VEGF or 0.5 nM C-peptide for predetermined times.

As can be seen, C-peptide increased ERK1/2 phosphorylation in a time-dependent manner, with a maximal stimulation at 15 min, and this ERK1/2 activation was maintained until 60 min (FIG. 3A).

Figure 3B:
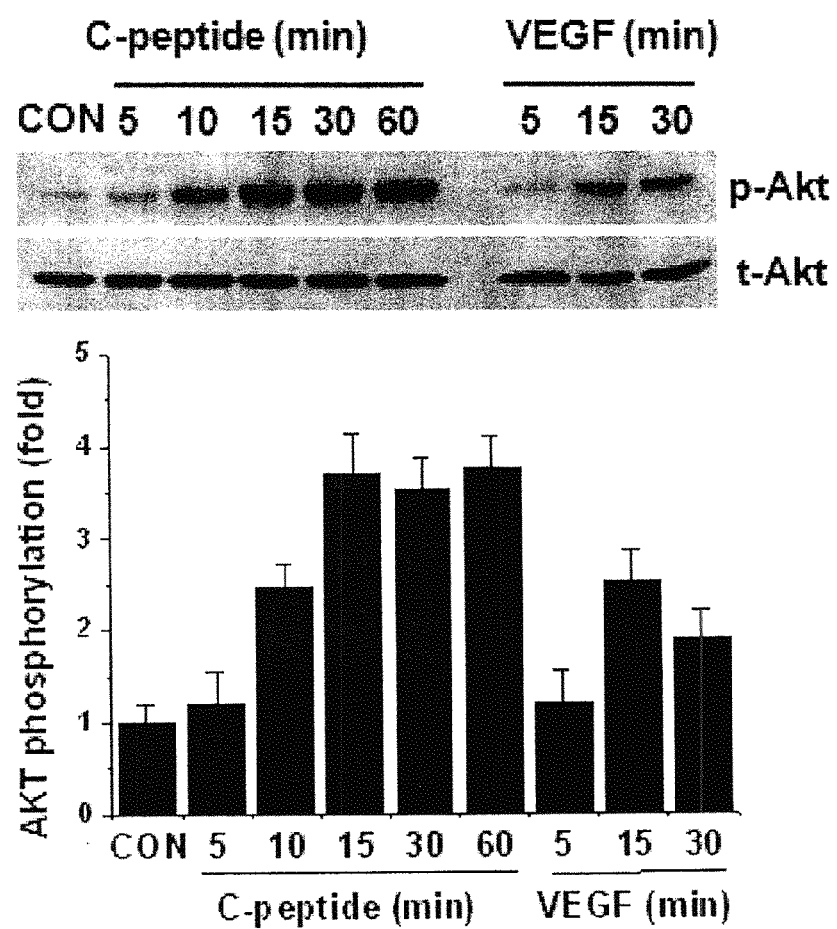
Figure 3C:
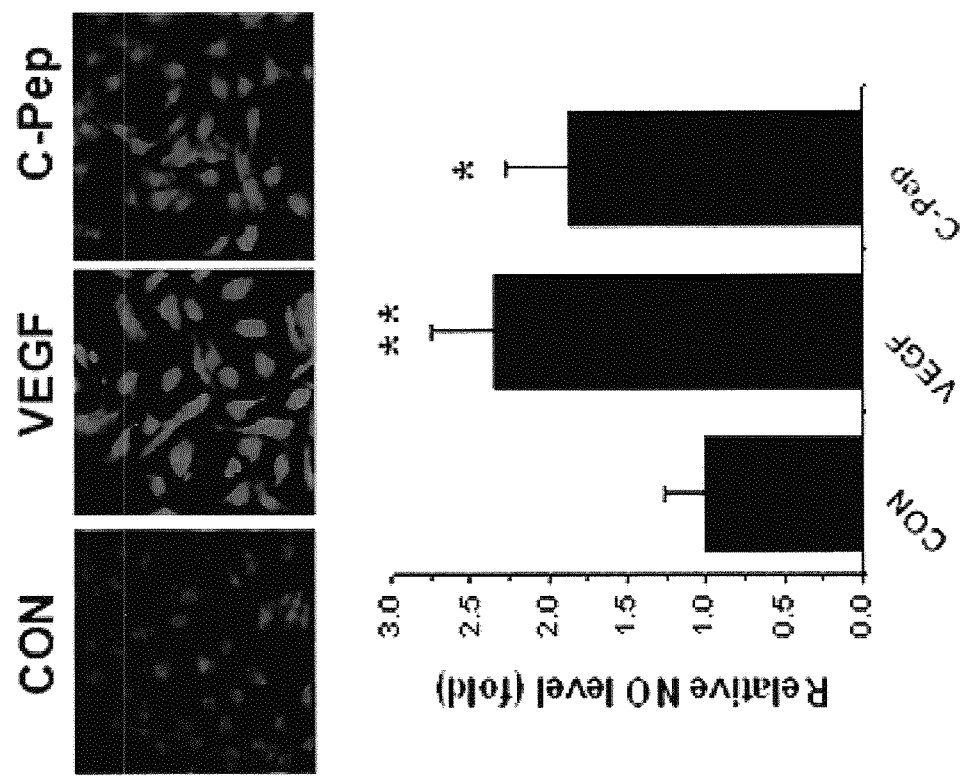
FIG. 3C shows results obtained after HUVECs are treated with 10 ng/ml VEGF or 0.5 nM C-peptide for 2 h and levels of intracellular NO are determined by confocal microscopy using a method known in the art. Results are expressed as mean±S.D. from three independent experiments. *p<0.05, **p<0.01.

Similarly, C-peptide induced a time-dependent phosphorylation of Akt, with a maximal effect at 15 min (FIG. 3B).

VEGF also induced the phosphorylation of ERK1/2 and Akt in a time-dependent manner (FIGS. 3A and 3B).

Example 5-2

Effect of C-Peptide on NO Production

Since phosphorylation of Akt increases NO production by VEGF, which is the important factor mediating angiogenesis, an examination was made to see whether C-peptide can stimulate NO production. For this, intracellular NO levels were measured using DAF-FM DA (diaminofluorescein-FM diacetate, Molecular Probes, Eugene, Oreg.) according to a method known in the art.

Briefly, HUVECs were treated with VEGF or C-peptide in phenol red-free low-serum media for indicated times and incubated with 2 μM DAF-FM DA for the final 1 h. Thereafter, the cells were washed with low-serum media before confocal microscropy. Levels of intracellular NO were determined by comparing the fluorescence intensities of treated cells with those of untreated control cells and expressing them as fold differences.

Treatment of HUVECs with C-peptide significantly elevated the level of intracellular NO (FIG. 3, $p<0.05$). A higher level of intracellular NO was also produced upon VEGF treatment ($p<0.01$).

Example 5-3

Roles of ERK1/2, PI3K/Akt, and NO Production in C-Peptide-Induced Angiogenesis

The roles of ERK1/2, PI3K/Akt, and NO in C-peptide-induced angiogenesis were examined using PD98059, wortmannin, and L-NG-nitroarginine methyl ester (L-NAME), respectively.

Figure 4A:
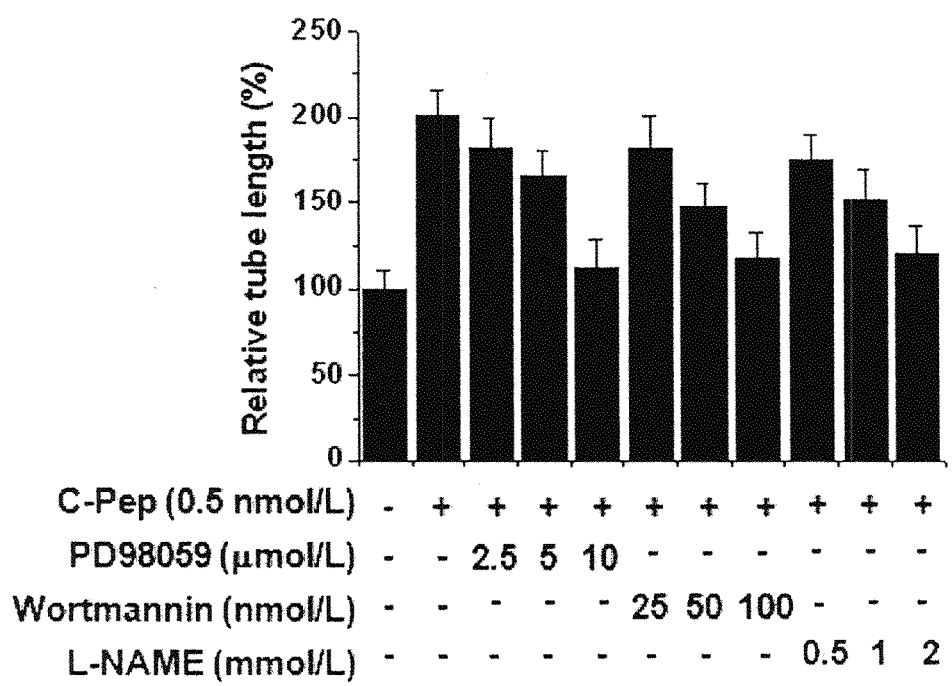
FIG. 4A is a graph in which tube formation is quantified by confocal microscopy and results are represented as mean±S.D. from three independent experiments after HUVECs were seeded onto a Matrigel layer and incubated for 24-30 h with 0.5 nM C-peptide (C-pep) in the presence of the indicated concentrations of L-NAME, PD98058, and wortmannin.

The C-peptide-stimulated tube formation by HUVECs was inhibited by PD98059, an ERK1/2 inhibitor, in a dose-dependent manner, with maximal inhibition at 10 μM. The PI3K/Akt inhibitor wortmannin and the NOS inhibitor L-NAME also exhibited dose-dependent inhibition of C-peptide-induced tube formation (FIG. 4A).

Figure 4B:
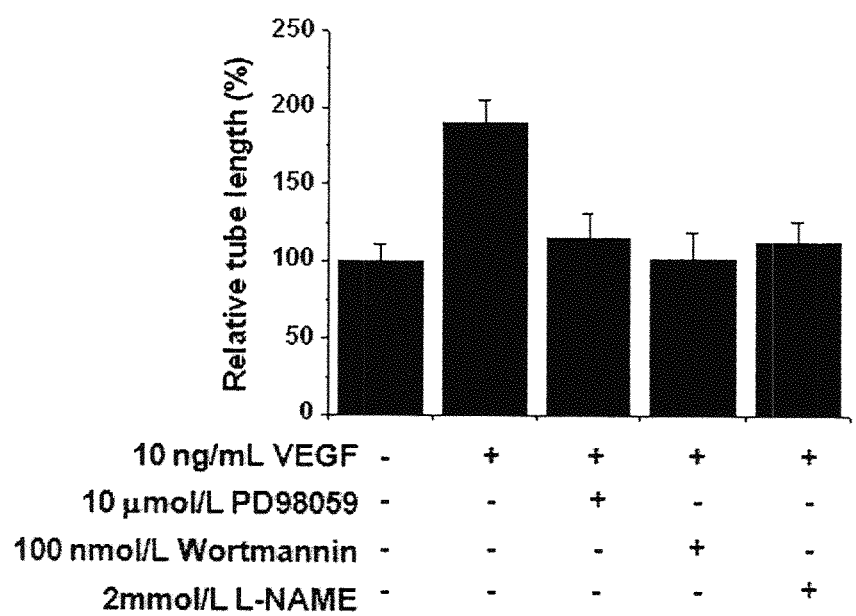
FIG. 4B is a graph in which tube formation is quantified by confocal microscopy and results are represented as mean±S.D. from three independent experiments after HUVECs were seeded onto a Matrigel layer and incubated for 24-30 h with 10 ng/ml VEGF in the presence of the indicated concentrations of L-NAME, PD98058, and wortmannin.

VEGF-induced tube formation was prevented by treatment with PD98059, wortmannin, and L-NAME (FIG. 4B).

Taken together, the data obtained above indicate that C-peptide stimulates angiogenesis via signaling pathways involving ERK1/2, PI3P/AKT, and NO production, and that signaling pathways involving ERK1/2, Akt, and NO production might be involved in C-peptide-induced angiogenesis.

Example 7

Therapeutic Effect of C-Peptide on Diabetic Wound Healing Impairment

Diabetic mice were generated by single intraperitoneal injection of a 100 mM citrate buffer (pH 4.5) containing streptozotocin in (150 mg/kg body weight). After injection, mice were supplied overnight with 10% sucrose to prevent sudden hypoglycemic shock. Sufficient hyperglycemia was observed two days after injection, as measured for blood glucose by the Accu-Check Active blood glucose monitor (Roch Diagnostics, Germany) and for glucosurea by Uriscan (TD Diagnostics, Young-In, Korea). After 1 week, mice with non-fasting blood glucose levels greater than 16 mM, polyuria, and glucosuria were defined diabetic and used for experiment. At two weeks after the streptozotocin injection, one group of diabetic mice was subcutaneously implanted with Alzet mini-osmotic pump 2004 (DIRECT, Cupertino, Calif.) containing C-peptide in PBS with a delivery rate of 35 pmol/kg/min for two weeks. The other diabetic and normal groups underwent sham operations.

The dorsal skin of the vertebral column was shaved with Veet cream before creating a wound. Full-thickness skin wounds, 4 mm in diameter, were created on the dorsal surface of the hind limbs with a biopsy punch, and closure was monitored with a digital camera. Open wound size was measured by tracing the wound margin using vernier calipers at regular intervals of two days, and monitored with a digital camera.

Figure 5A:
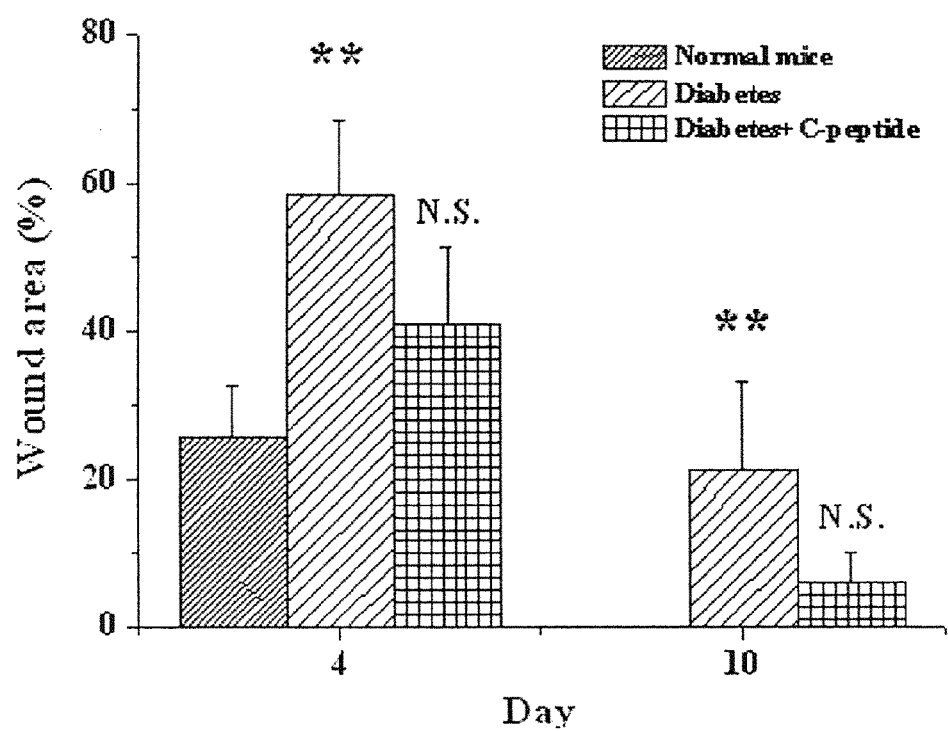
FIG. 5A is a graph in which comparison among the wound healing of healthy (healthy; n=12 per group), diabetic mice (diabetic; n=12 per group) and C-peptide-administrated diabetic mice (diabetic+C-pep; n=12 per group) is made at 4 and 12 d after skin injury. **, p<0.01, N.S. no significant difference.

To determine whether C-peptide can induce wound closure in diabetic mice, C-peptide was administered continuously at a delivery rate of 35 pmol/kg/min with subcutaneous osmotic minipumps implanted under the diabetic mice. Wounds, 4 mm in diameter, were created on the dorsal surface of the hind limb in normal, diabetic and C-peptide administrated diabetic mice (STZ-induced diabetes for 4 weeks). Wounds diabetic mice had exhibited a significantly slower healing rate than those of normal mice. However, in diabetic mice supplemented with C-peptide using osmotic pumps, no significant differences in wound area were observed from 4 and 10 days after skin injury (FIG. 5A). Comparisons among the wound area of the normal, diabetic and C-peptide administrated diabetic mice showed significantly differences on 4 and 10 d (FIG. 5B).

Example 8

C-Peptide Activation of Fibroblast Cell Migration

Figure 6A:
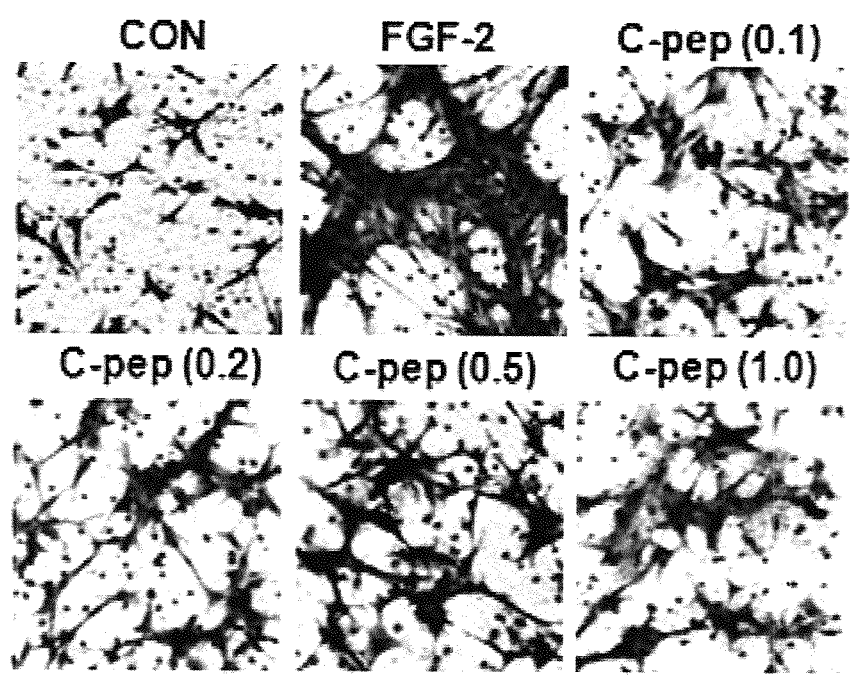
Figure 6B:
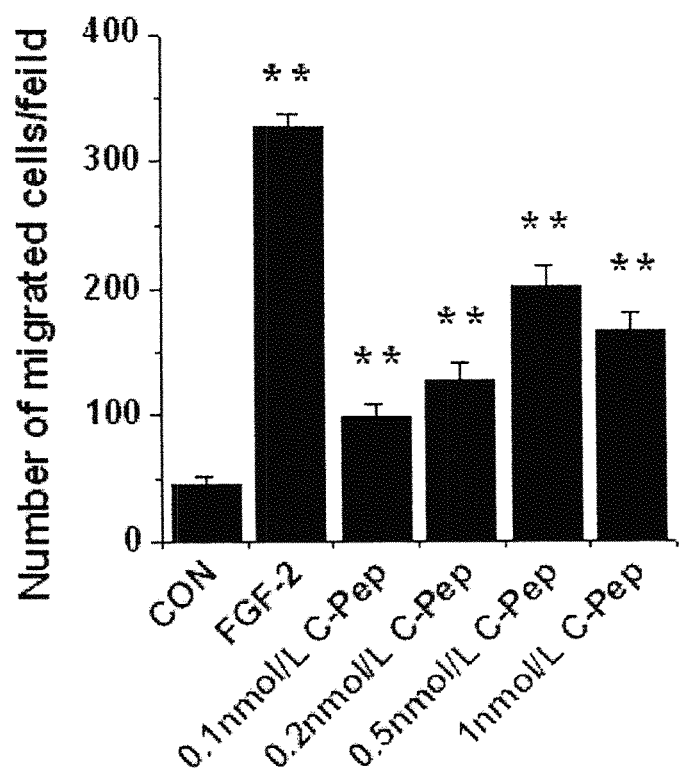
FIG. 6B is a graph in which chemotactic migration is quantified by counting the migrated cells (n=3)

To elucidate the role of C-peptide in the migration of chemotactic fibroblast cells, NIH3T3 cells were treated with C-peptide for 12 h. C-peptide induced a dose-dependent increase in the chemotactic migration of fibroblast cells, with a maximal effect at 1 nM (FIGS. 6A and 6B).

Figure 6C:
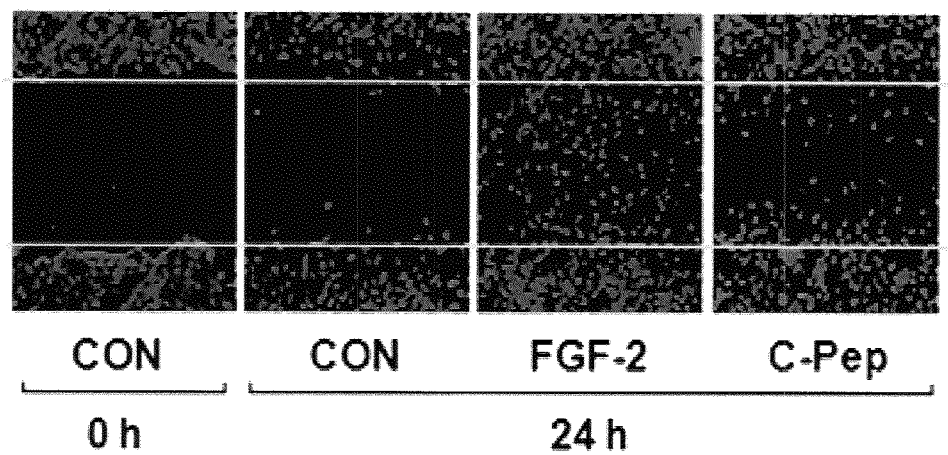
FIG. 6C shows confocal microscopic images of confluent cell layers which were wounded and incubated with 1 ng/ml FGF-2 or 0.5 nM C-peptide for 24 h.
Figure 6D:
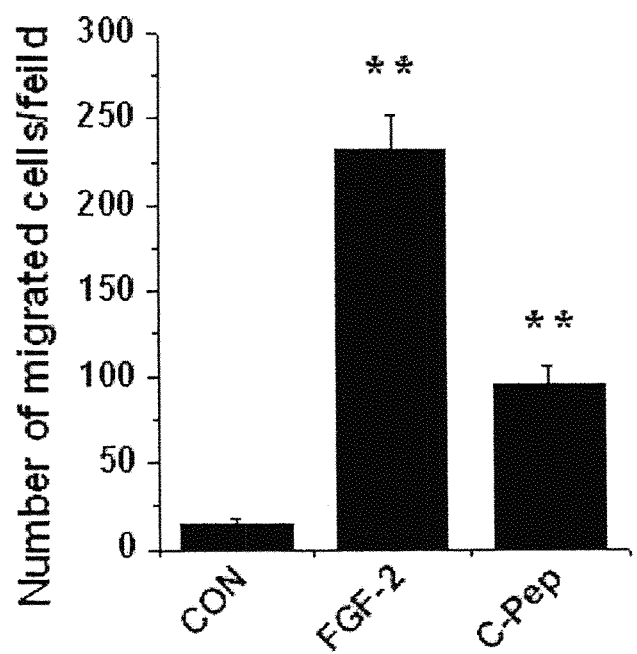
FIG. 6D is a graph in which cell migration is quantified by counting cells that migrated to the scratched area (n=3).

C-peptide-induced cell migration was further investigated by the wound-healing assay. C-peptide (0.5 nM) significantly stimulated cell migration to the wounded area ($p<0.01$; FIGS. 6C and 6D). FGF-2 also stimulated chemotactic migration and wound healing in fibroblast cells ($p<0.01$; FIG. 6). Hence, C-peptide stimulates fibroblast cell migration, which is essential for wound-healing process in injured skin.

Example 9

C-Peptide Stimulation of Hair Follicle Regeneration and Blood Vessel Formation

The effect of C-peptide on the regeneration of hair follicles and the formation of blood vessels was observed by whole-mount immunostaining. In this regard, 14 days after wounding, mice were sacrificed, and the dorsal skin was removed for observation of hair follicles and blood vessels. Skin tissues from all the dead mice were excised using a scissor in order to avoid damaging its healing edge, fixed immediately in 4% paraformaldehyde in PBS overnight, and stored overnight in methanol at −20° C. For immunohistochemistry, tissue samples were blocked with 2% BSA in 0.1% TritonX-100 in TBS, and incubated with goat-polyclonal platelet endothelial cell adhesion molecule-I antibody for 2 d, followed by probing with Alexa-546-conjugated rabbit anti-goat IgG and then confocal microscopy.

Figure 7A:
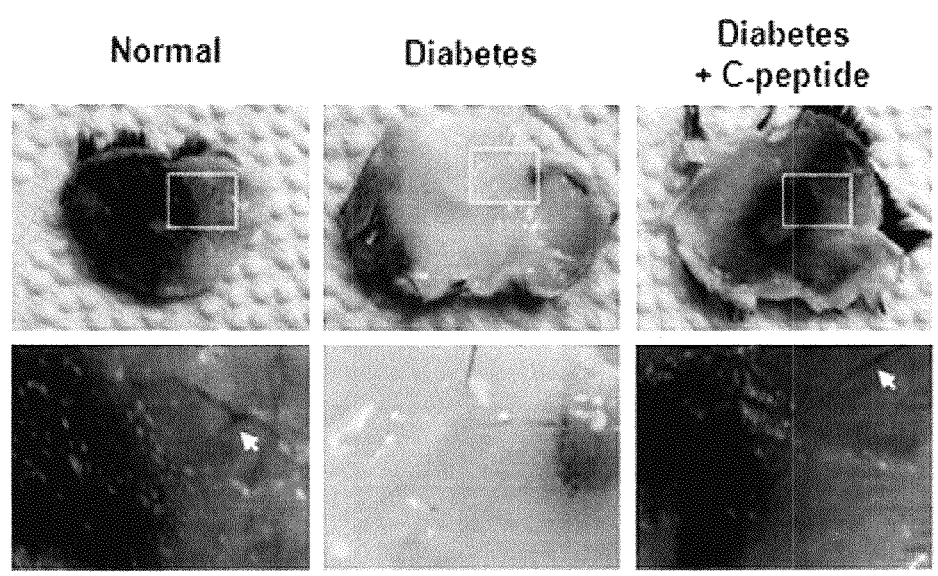
FIG. 7A shows representative photographs of removed the dorsal skin of hind limb from normal (n=6), diabetic (n=6), and diabetic+C-peptide (n=6) in which the square areas are displayed as magnified images at the bottom of each image. Hair follicles and blood vessels were developed in the Normal and Diabetic+C-peptide but not in the Diabetic (indicated by arrows)
Figure 7B:
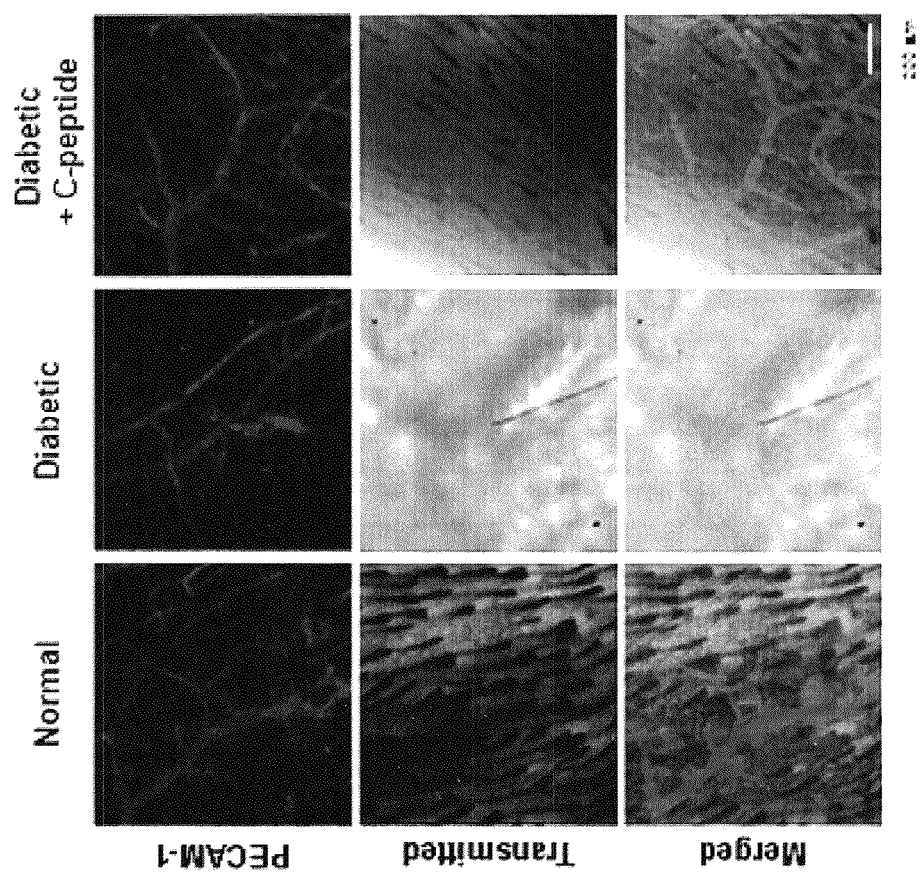
FIG. 7B shows images of blood vessels visualized with PECAM-1 antibody (Upper panel) and hair follicles visualized in the dorsal skin (middle panel). C-peptide increased number of hair follicles and blood vessels. Scale bar=200 mm.
Figure 8:
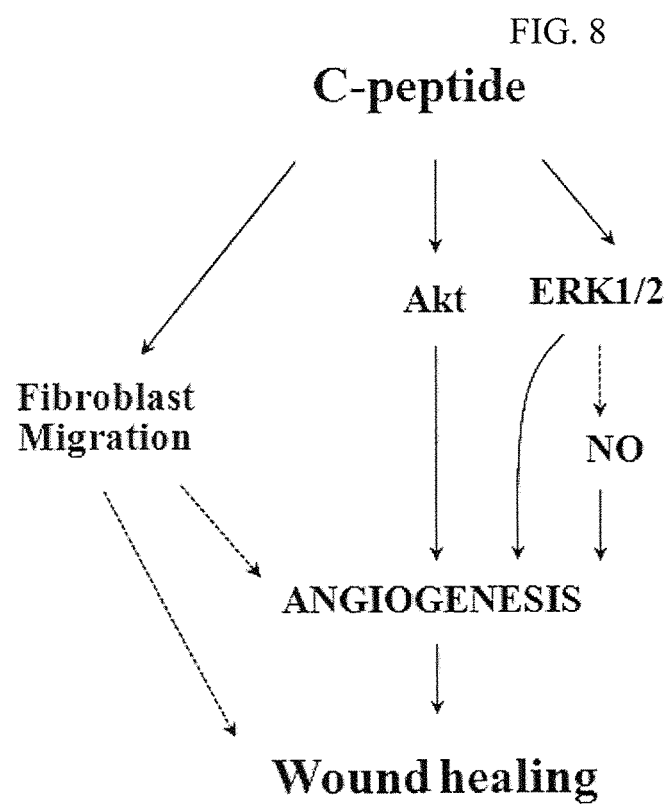
FIG. 8 is a diagram showing a possible signaling pathway of C-peptide-induced angiogenesis and prevention of diabetes-impaired wound healing, suggesting that C-peptide activates angiogenesis via pathways involving ERK1/2, Akt, and NO production and improves delayed wound healing by enhancing angiogenesis.

The results are shown in FIG. 7. The number of hair follicles and blood vessels in the subcutaneous tissue surrounding the wounds of diabetic mice was significantly lower than in the normal mice as evaluated from photo (FIG. 6A) and by PECAM-1 staining (FIG. 6B). C-peptide administrated mice skin showed a significant increase regeneration of hair follicle and formation of blood vessel with concomitantly accelerated wound closure compared with those diabetic mice.

These results suggest a potential therapeutic value of C-peptide for treating diabetes-delayed wound healing, especially in diabetic patients with impaired microcirculation.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treatment of impaired angiogenesis caused by diabetes in a human in need thereof, comprising administering a dose of between 2.4 µg and 60 µg of C-peptide to induce at least one of chemotactic migration of endothelial cells, cell migration to wounded areas, capillary-like network formation, extracellular signal-regulated kinases (ERK) 1/2 phosphorylation, Akt phosphorylation, and nitric oxide (NO) production in said human.

2. The method of claim 1, wherein the C-peptide has the amino acid sequence selected from the group consisting of SEQ ID NOS: 1 and 3.

3. The method of claim 1, wherein the impaired angiogenesis caused by diabetes comprises an ulcer.

4. The method of claim 3, wherein the ulcer is a foot ulcer.

5. The method of claim 4, wherein the impaired angiogenesis caused by diabetes further comprises one or more of stroke, renal disease, and cardiac disease.

6. The method of claim 1, comprising administering C-peptide in a concentration of between about 0.1 nM and about 1.0 nM.

7. The method of claim 6, comprising administering C-peptide in a concentration of about 0.5 nM.

8. The method of claim 1, comprising administering the C-peptide in a dose of about 18 µg.

9. The method of claim 1, comprising administering the C-peptide at a rate of between about 1.45 pmol/kg/min and about 36.5 pmol/kg/min.

10. The method of claim 1, comprising administering the C-peptide via an intradermal route.

11. A method for treatment of diabetic wound healing impairment in a human in need thereof, comprising administering dose of between 2.4 µg and 60 µg of C-peptide to induce at least one of chemotactic migration of endothelial cells, cell migration to wounded areas, capillary-like network formation, and extracellular signal-regulated kinases (ERK) 1/2 and Akt phosphorylation and nitric oxide (NO) production in said human.

12. The method of claim 11, wherein the C-peptide has the amino acid sequence selected from the group consisting of SEQ ID NOS: 1 and 3.

13. The method of claim 11, wherein the diabetic wound healing impairment is selected from the group consisting of strokes, renal diseases, cardiac diseases, and foot ulcers.

* * * * *

```
                          SEQUENCE LISTING

<160> NUMBER OF SEQ ID NOS: 7

<210> SEQ ID NO 1
<211> LENGTH: 31
<212> TYPE: PRT
<213> ORGANISM: Homo sapiens

<400> SEQUENCE: 1

Glu Ala Glu Asp Leu Gln Val Gly Gln Val Glu Leu Gly Gly Gly Pro
 1               5                  10                  15

Gly Ala Gly Ser Leu Gln Pro Leu Ala Leu Glu Gly Ser Leu Gln
             20                  25                  30

<210> SEQ ID NO 2
<211> LENGTH: 31
<212> TYPE: PRT
<213> ORGANISM: Rattus norvegicus

<400> SEQUENCE: 2

Glu Val Glu Asp Pro Gln Val Pro Gln Leu Glu Leu Gly Gly Gly Pro
 1               5                  10                  15

Glu Ala Gly Asp Leu Gln Thr Leu Ala Leu Glu Val Ala Arg Gln
             20                  25                  30

<210> SEQ ID NO 3
<211> LENGTH: 31
<212> TYPE: PRT
<213> ORGANISM: Pan troglodytes

<400> SEQUENCE: 3

Glu Ala Glu Asp Leu Gln Val Gly Gln Val Glu Leu Gly Gly Gly Pro
 1               5                  10                  15

Gly Ala Gly Ser Leu Gln Pro Leu Ala Leu Glu Gly Ser Leu Gln
             20                  25                  30

<210> SEQ ID NO 4
<211> LENGTH: 29
<212> TYPE: PRT
<213> ORGANISM: Mus musculus

<400> SEQUENCE: 4

Glu Val Glu Asp Pro Gln Val Glu Gln Leu Glu Leu Gly Gly Ser Pro
 1               5                  10                  15

Gly Asp Leu Gln Thr Leu Ala Leu Glu Val Ala Arg Gln
             20                  25

<210> SEQ ID NO 5
<211> LENGTH: 26
<212> TYPE: PRT
<213> ORGANISM: Bos taurus

<400> SEQUENCE: 5

Glu Val Glu Gly Pro Gln Val Gly Ala Leu Glu Leu Ala Gly Gly Pro
 1               5                  10                  15

Gly Ala Gly Gly Leu Glu Gly Pro Pro Gln
             20                  25
```

```
<210> SEQ ID NO 6
<211> LENGTH: 21
<212> TYPE: PRT
<213> ORGANISM: Turdus merula

<400> SEQUENCE: 6

Ser Gly Pro Leu His Gly Glu Leu Gly Glu Leu Pro Phe Gln Gln Glu
 1               5                  10                  15

Glu Phe Glu Lys Val
            20

<210> SEQ ID NO 7
<211> LENGTH: 21
<212> TYPE: PRT
<213> ORGANISM: Sula sula

<400> SEQUENCE: 7

Ser Gly Pro Leu His Gly Glu Val Gly Glu Leu Pro Phe Gln Gln Glu
 1               5                  10                  15

Glu Phe Glu Lys Val
            20
```